US011065440B2

United States Patent
Laudanski

(10) Patent No.: US 11,065,440 B2
(45) Date of Patent: Jul. 20, 2021

(54) HEARING ASSISTANCE DEVICE COMPRISING AN IMPLANTABLE PART

(71) Applicant: Oticon Medical A/S, Smørum (DK)

(72) Inventor: Jonathan Laudanski, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 323 days.

(21) Appl. No.: 15/793,450

(22) Filed: Oct. 25, 2017

(65) Prior Publication Data

US 2018/0043161 A1 Feb. 15, 2018

Related U.S. Application Data

(62) Division of application No. 14/750,338, filed on Jun. 25, 2015, now Pat. No. 9,839,779.

(30) Foreign Application Priority Data

Jun. 26, 2014 (EP) .................................... 14174318

(51) Int. Cl.
*A61N 1/36* (2006.01)
*A61N 1/05* (2006.01)

(52) U.S. Cl.
CPC ......... *A61N 1/0529* (2013.01); *A61N 1/0541* (2013.01); *A61N 1/3606* (2013.01); *A61N 1/36038* (2017.08); *A61N 1/36039* (2017.08)

(58) Field of Classification Search
CPC .............. A61N 1/36032; A61N 1/0541; A61N 1/0529; A61N 1/3606; A61N 1/3605; A61N 1/05; A61N 1/08; A61N 1/36146; H04R 25/606; A61B 5/04845; A61B 5/121; A61B 5/12; A61B 5/486; A61B 5/6803;
(Continued)

(56) References Cited

U.S. PATENT DOCUMENTS

| | | | |
|---|---|---|---|
| 4,207,441 | A | 6/1980 | Ricard et al. |
| 4,532,930 | A | 8/1985 | Crosby et al. |

(Continued)

FOREIGN PATENT DOCUMENTS

| | | |
|---|---|---|
| EP | 0 198 618 A2 | 10/1986 |
| EP | 2 586 491 A1 | 5/2013 |

OTHER PUBLICATIONS

Bal et al., "Potassium Currents in Octopus Cells of the Mammalian Cochlear Nucleus," Journal of Neurophysiology, vol. 86, Nov. 2001, pp. 2299-2311, (Journal of Neurophysiology, vol. 92, 2004 pp. 1263).

*Primary Examiner* — Deborah L Malamud
(74) *Attorney, Agent, or Firm* — Birch, Stewart, Kolasch & Birch, LLP

(57) ABSTRACT

A hearing assistance device comprises an implantable part for electrically stimulating an auditory nerve of a user. The implanted part comprises a) a current source generator; and b) an electrode array configured to be located inside one of the cochlear scala or adjacent to the auditory nerve. The hearing assistance device is configured to produce a time-varying waveform delivered by the current source generator, the time-varying waveform comprising a positively sloping positive pulse. This has the advantages of providing a smaller spatial spread of neurons being discharged by electric stimuli from a given electrode. The invention may e.g. be used in cochlear implant hearing assistance devices.

10 Claims, 12 Drawing Sheets

(58) Field of Classification Search
CPC ............. A61B 5/686; A61B 2576/026; A61B 5/4836; A61B 7/04; G06F 3/015; G06F 19/3406
See application file for complete search history.

(56) References Cited

U.S. PATENT DOCUMENTS

| | | | | |
|---|---|---|---|---|
| 6,175,767 | B1 * | 1/2001 | Doyle, Sr. .......... | A61N 1/36036 607/57 |
| 6,631,295 | B2 | 10/2003 | Rubinstein et al. | |
| 7,702,396 | B2 | 4/2010 | Litvak et al. | |
| 8,036,754 | B2 * | 10/2011 | Lee .................... | A61N 1/36017 607/72 |
| 8,346,368 | B2 | 1/2013 | Killian | |
| 2005/0222644 | A1 | 10/2005 | Killian et al. | |

* cited by examiner

HEARING ASSISTANCE DEVICE COMPRISING AN IMPLANTABLE PART

CROSS-REFERENCE TO RELATED APPLICATIONS

This application is a Divisional of copending application Ser. No. 14/750,338, filed on Jun. 25, 2015, which claims priority under 35 U.S.C. § 119(a) to Application No. 14174318.7, filed in the European Patent Office on Jun. 26, 2014, all of which are hereby expressly incorporated by reference into the present application.

TECHNICAL FIELD

The present application relates to hearing assistance devices and methods of stimulating the auditory system, in particular to electrical stimulation of the cochlear nerve. The disclosure relates specifically to a hearing assistance device comprising an implantable part for electrically stimulating an auditory nerve of the user.

The application furthermore relates to a method of operating a hearing assistance device, the hearing assistance device comprising an implantable part.

The application further relates to a data processing system comprising a processor and program code means for causing the processor to perform at least some of the steps of the method.

The scheme for providing an appropriate stimulation waveform outlined in the present disclosure may be generally applicable to electric nerve stimulation. Embodiments of the disclosure may e.g. be useful in applications such as cochlear implant hearing assistance devices.

BACKGROUND

The following account of the background relates to one of the areas of application of the present application, hearing aids for electrical stimulation of the cochlear nerve, typically termed 'cochlear implant hearing (assistance) devices' or simply 'cochlear implants' (CI). Cochlear implant hearing assistance devices have been known in many years in a variety of configurations, but typically comprising a) a number of electrodes implantable in different locations of the cochlea allowing a stimulation of different frequencies of the audible range, b) an external part for picking up and processing sound from the environment, and for determining sequences of pulses for stimulation of the electrodes in dependence on the current input sound, c) a (typically wireless, e.g. inductive) communication link for simultaneously transmitting information about the stimulation sequences and for transferring energy to d) an implanted part allowing the stimulation to be generated and applied to the relevant of said electrodes.

Such systems are e.g. described in U.S. Pat. No. 4,207,441 and in U.S. Pat. No. 4,532,930.

A cochlear implant electrically stimulates the auditory nerve of a deaf patient to produce a sound perception. The CI-devices typically have between 12 and 24 processing channels which encode the sound energy level at different cochlear locations. Due to electrical current spread within the scala tympani (i.e. the cochlear duct in which the electrode array lies), the spectral resolution is reduced and therefore the speech perception performance of cochlear implant patients does not improve when the number of activated channels is increased higher than appr. 8 to 12. This is in contrast to normally hearing listeners which benefit from an increasing number of processing channels in psycho-acoustic studies using speech vocoders.

The problem is well-known and different solutions have been envisioned to solve it. Most of the work has been concerned with focusing current using multi-polar stimulation. This current focussing technic relies on a general principle of beam-forming using multiple sources. Beam-forming is used in various technologies such as radar or microphone array. The results of current focussing have been disappointing for different reasons. First, power consumption grows linearly with the number of channels used. Second focusing the electric field can have subtle sub-threshold effects from the side-lobe producing the focus. Because of these drawbacks, other works to reduce the spread of excitation are on-going. Recently another approach has been to use optical stimulation produced by laser pulses in the infra-red range. This new stimulation technique may not have the same level of spreading but is still currently very power consuming.

SUMMARY

The present disclosure describes a scheme for focussed neural excitation based on the temporal shape of stimulating waveform.

The proposed solution relies on the use of specifically designed pulse shapes, which preferably interact with the dynamics of ionic channels to only activate a limited region of neurons around the stimulation site.

Typically, prior art electrical stimulating pulses have a square shape, which implies that the current rises instantaneously (or near instantaneously as limited by physical properties of the device and media). The effect of the pulse is stronger in front of the electrode, and the strength of the stimulation decreases with distance to the stimulation electrode. One should note that from the point of view of the farther away neurons, only the amplitude of the square shape pulses changes.

For pulses with different shapes such as triangular pulses, or any pulse with a ramp, as proposed in the present disclosure, not only the amplitude of the pulse changes (with distance), so does the slope of the ramp. More specifically, the further away the neuron the shallower the rising slopes of the stimulation seen by the neuron.

One has to know that certain ionic channels preclude neurons from discharging if the rate of depolarization of the membrane is slower than a certain "slope-threshold". This effect has been observed in many neurons of the auditory systems (see e.g. [Bal & Oertel; 2001]). In that case, the effect is due to the presence of the (low voltage activated) potassium (K+) current $I_{KLVA}$. But other ionic currents may react in specific fashions to the temporal shape of the stimulation waveform.

The solution to the problem above mentioned is to reduce the spread of excitation by using the interaction from temporal shape of a stimulation waveform and the dynamics of ionic channels. Narrowing the spatial extent of the field of excitation in that way is simple and efficient since it does not rely on the addition of other current sources, which would imply extra power consumption.

Furthermore, one may bio-engineer the neuron, either genetically or pharmacologically to express or produce specific ionic channels that enhance or reduce this effect depending on the desired outcome.

An object of the present application is to improve the electrical stimulation of the cochlear nerve by a cochlear implant hearing assistance device.

Objects of the application are achieved by the invention described in the accompanying claims and as described in the following.

A Hearing Assistance Device:

In an aspect of the present application, an object of the application is achieved by A hearing assistance device comprising an implantable part for electrically stimulating an auditory nerve of a user. The implanted part comprises

- a current source generator;
- an electrode array configured to be located inside one of the cochlear scala or adjacent to the auditory nerve, or at the auditory brainstem;
- the hearing assistance device being configured to produce a time-varying waveform delivered by said current source generator, said time-varying waveform comprising a positively sloping positive pulse.

This has the advantages of providing a smaller spatial spread of neurons being discharged by electric stimuli from a given electrode.

In the present context, the term 'positively sloping positive pulse' is intended to indicate that the waveform comprises a positive pulse, which is deliberately non-square in that it comprises a segment having a positive slope (or a finite positive tangent) followed by a falling edge. Further a positively sloping pulse is intended to include a non-linear, e.g. a piece-wise linear, section (e.g. comprising a number of small rising and flat phases or steps), or a section exhibiting a (e.g. monotonous) continuous functional course (e.g. exponential or logarithmic) that on a macroscopic scale provide an increase in amplitude over the width of the positively sloped pulse.

This has the advantage of enabling a modulation of either the nerve discharge probability or the nerve discharge temporal accuracy, or both at the same time. In particular, a narrower spatial excitation without the requirement of extra current sources (which require energy to "focus" or "steer" the electric field pattern) may advantageously be provided by embodiments of the present disclosure.

In an embodiment, the time-varying waveform comprising a positively sloping positive pulse comprises a (first) rising edge and a (second) falling edge, wherein the height of the falling edge is larger than the height of the rising edge. In an embodiment, the time-varying waveform comprises a rising edge followed by a substantially monotonically increasing segment followed by a falling edge. In an embodiment, the rising edge has a positive slope that is larger than the slope of the intermediate segment, such as at least twice or at least 5 times as large. In an embodiment, the time-varying waveform comprises a rising edge followed by an intermediate segment followed by a falling edge, wherein the height of the first (rising) edge is smaller than the height of the second (falling) edge. In an embodiment, the height of the rising edge is substantially zero. In an embodiment, the positive pulse is substantially triangular.

In an embodiment, the time-varying waveform comprises a bi-phasic sloping, symmetric waveform stimulation pulse. In an embodiment, the time-varying waveform comprises a negatively sloping negative pulse. In an embodiment, the negatively sloping negative pulse comprises a first edge and a second edge, wherein the height of the first edge is smaller than the height of the second edge.

In an embodiment, the hearing assistance device is configured to dynamically adapt the time-varying waveform to the current input signal (e.g. comprising sound from the environment or audio signals directly received from an audio source). In an embodiment, the hearing assistance device is configured to vary the slope of the positively sloping positive pulse in dependence of the current input signal. In an embodiment, some of the electrodes of the multi-electrode array are stimulated with time-varying waveforms comprising a sloping positive pulse while other electrodes of the multi-electrode array are stimulated with time-varying waveforms comprising other waveforms, e.g. a square positive pulse. In an embodiment, one or more specific of the electrodes of the multi-electrode array is/are stimulated with time-varying waveforms comprising a sloping positive pulse while in first time segments, while being stimulated with time-varying waveforms comprising other waveforms, e.g. a square positive pulse in second time segments. In an embodiment, said first and second time segments are determined (such as dynamically determined) according to the current input signal (e.g. its character, speech, music, noise, etc.). In an embodiment, said first and second time segments are determined according to the current acoustic environment. This has the advantage of enabling different properties of sound to be assigned different strategies for being "transferred" to the user.

In an embodiment, the hearing assistance device is configured to dynamically adapt the time-varying waveform to the current input signal, e.g. to optimize (provide a smaller) power consumption compared to using square pulses.

In an embodiment, the hearing assistance device is configured to provide that the time-varying waveform stimulation pulse is modulated in width according to the frequency content of a current input signal. In other words, the larger the energy content of a current input signal in a given frequency range and in a given time slot, the wider the time-varying waveform stimulation pulse. In an embodiment, the hearing assistance device is configured to provide that the time-varying waveform stimulation pulse is modulated in amplitude according to the frequency content of a current input signal. In other words, the larger the energy content of a current input signal in a given frequency range and in a given time slot, the larger the amplitude of the time-varying waveform stimulation pulse. In an embodiment, the hearing assistance device is configured to provide that the time-varying waveform stimulation pulse is modulated in width as well as amplitude according to the frequency content of a current input signal.

In an embodiment, the current source generator is configured to deliver a spatio-temporal current waveform using one or more current sources in which the temporal pattern is adapted to evoke a pre-defined spatial excitation pattern (i.e. a spatial pattern of neural response probability or spatial pattern of neural jitter). The temporal pattern can be adapted either in an on-line (during operation of the hearing assistance device) or off-line method.

In an embodiment, the hearing assistance device comprises a multi electrode array e.g. in the form of a carrier comprising a multitude of electrodes adapted for being located in the cochlea in proximity of an auditory nerve of the user. The carrier is preferably flexible to allow a proper positioning of the electrodes in cochlea to achieve that the electrodes can be inserted in cochlea. Preferably, the individual electrodes are spatially distributed along the length of the carrier to provide a corresponding spatial distribution along the cochlear nerve in cochlea when the carrier is inserted in cochlea.

When the implanted part is operationally implanted in a person, the electrodes are preferably located fully or partially in the cochlea of the person in a way allowing the electric stimulation signal to be applied to the auditory nerve and allowing a response signal to said stimulation (potentially) comprising a response from the nerve to be measured. Alternatively or additionally, the electrodes may be located at the auditory brainstem (to thereby allow the hearings assistance device to pick up evoked brainstem responses, e.g. electrically evoked auditory brain stem responses (eABRs)).

In an embodiment, the hearing assistance device consists of one fully implanted part only.

In an embodiment, the hearing assistance device comprises at least one external part and a communications link configured to allow exchange of data between the external and implanted parts of the device.

In an embodiment, the hearing assistance device comprises a reference electrode adapted for being located outside the cochlea. In an embodiment, the hearing assistance device (e.g. the control unit) is configured to provide that the stimulation electrode is the same as the recording electrode. In an embodiment, the hearing assistance device (e.g. the control unit) is configured to provide that the stimulation electrode and the recording electrode are two physically different entities.

In an embodiment, the hearing assistance device comprises more than one electrode array. Examples of such could be 1) a binaural case, where two arrays (one for each of the two ears within the same device) are stimulated by the same processor, or 2) a multi-array case (for ossified cochleas), where several (short) electrode-arrays are used for one cochlea.

In an embodiment, the hearing assistance device is adapted to provide a frequency dependent gain to compensate for a hearing loss of a user. In an embodiment, the hearing assistance device comprises a signal processing unit for enhancing the input signals and providing a processed output signal. Various aspects of cochlear implant hearing assistance devices are described in [Clark; 2003].

In an embodiment, the hearing assistance device comprises an input transducer for converting an input sound to an electric input signal. In an embodiment, the hearing assistance device comprises a directional microphone system adapted to enhance a target acoustic source among a multitude of acoustic sources in the local environment of the user wearing the hearing assistance device. In an embodiment, the directional system is adapted to detect (such as adaptively detect) from which direction a particular part of the microphone signal originates. This can be achieved in various different ways as e.g. described in the prior art.

In an embodiment, the hearing assistance device comprises an antenna and transceiver circuitry for wirelessly receiving a direct electric input signal from another device, e.g. a communication device or another hearing assistance device. In an embodiment, the hearing assistance device comprises a (possibly standardized) electric interface (e.g. in the form of a connector) for receiving a wired direct electric input signal from another device, e.g. a communication device or another hearing assistance device. In an embodiment, the direct electric input signal represents or comprises an audio signal and/or a control signal and/or an information signal.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 40 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 μs, for $f_s$=20 kHz. In an embodiment, a number of audio samples are arranged in a time frame. In an embodiment, a time frame comprises 64 audio data samples. Other frame lengths may be used depending on the practical application.

In an embodiment, the hearing assistance devices comprise an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In an embodiment, the hearing assistance device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing assistance device is split into a number NI of frequency bands, where NI is e.g. larger than 5, such as larger than 10, such as larger than 50, such as larger than 100, such as larger than 500, at least some of which are processed individually. In an embodiment, the hearing assistance device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing assistance device comprises a number of detectors of the characteristics of the current input signal (e.g. one or more of level, frequency content, modulation, reverberation, voice content, noise content, auto-correlation, music, etc.). In an embodiment, the hearing assistance device comprises a classification unit for classifying a current acoustic environment and/or the current input signal (e.g. fully or partially based on detectors of the characteristics of the current input signal).

In an embodiment, the hearing assistance device comprises a level detector (LD) for determining the level of an input signal (e.g. on a band level and/or of the full (wide band) signal). The input level of the electric microphone signal picked up from the user's acoustic environment is e.g. a classifier of the environment. In an embodiment, the level detector is adapted to classify a current acoustic environment of the user according to a number of different (e.g. average) signal levels, e.g. as a HIGH-LEVEL or LOW-LEVEL environment.

In an embodiment, the hearing assistance device further comprises other relevant functionality for the application in question, e.g. compression, noise reduction, etc.

In an embodiment, the hearing assistance device comprises a cochlear implant hearing device.

Use:

In an aspect, use of a hearing assistance device as described above, in the 'detailed description of embodiments' and in the claims, is moreover provided.

A Method of Operating a Hearing Assistance Device:

In an aspect, A method of operating a hearing assistance device, the hearing assistance device comprising an implantable part is furthermore provided by the present application. The method comprises providing an electrode array comprising one or more stimulation electrodes configured to be located inside one or more stimulation electrodes configured to be located inside one of the cochlear scala or adjacent to the auditory nerve, or at the auditory brainstem;

providing stimulation current to generate electric stimulation pulses to one or more of said stimulation electrodes;

using said stimulation current to provide a parameterized time-varying waveform of said electric stimulation pulses to one or more of said stimulation electrodes, said parameterized time-varying waveform comprising a positively sloping positive pulse.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

In an embodiment, the method comprises providing a model of ionic currents present in a nerve or neuron, from which the temporal pattern of current to deliver can be computed so that a specific discharge probability and/or temporal accuracy can be obtained.

In an embodiment, the method comprises one or more of the following steps:

Computing a first passage time probability density using a model of said parameterized time-varying waveform.

Computing a set of fibres, which are activated by a single pulse of said parameterized time-varying waveform.

Computing interactions between sub-sequent pulses in a pulse train of said parameterized time-varying waveforms.

This allows a method of enhancing or creating or modifying the expression of specific ionic channels in the neurons, which should be stimulated so that the efficiency of the temporal waveform of stimulation may be modified or modulated in a positive or negative manner.

The method may further facilitate one or more of the following:

a stimulation strategy in which the probability of discharge is modulated using a parameterized pulse shape specifically designed to limit the spread of excitation;

a stimulation strategy in which the parameter of the pulse-shape is modulated to produce a specific excitation pattern by acting on either the spread of excitation or the discharge probability or the discharge latency;

a fitting procedure by which a clinician/audiologist or the patient himself (for example through the use of custom software) estimates the extent of the spread of excitation using the feed-back from the patient. A number of different parameterized time-varying waveforms may be used as electric stimulation pulses and the user's response thereto recorded. Preferably, the user responses for a number of identical stimulation pulses ('played' at different times) are recorded and averaged.

In an embodiment, the method comprises the provision of a subjective measure related to the use of a masking paradigm in which the patient is asked to detect the presence of a target stimulation in concurrence with a masker presented simultaneously or earlier. The method may rely on a loudness matching method where the loudness perceived is compared between pulses of differing parameterized waveforms. The fitting method may rely on a loudness categorisation task where the subject is asked to attribute a loudness category located on a loudness scale for pulses with parameterized pulse-shapes.

In an embodiment, the method comprises a fitting procedure, wherein an objective measure for fitting the pulse-shape is provided, said objective measure being based on recording the nerve response after its stimulation or any evoked neural response produced by the stimulation.

In an embodiment, the method comprises exposing neurons of the user to genetic or pharmacological treatment prior to or during use of the hearing assistance device to express or produce specific ionic channels that enhance or reduce this effect depending on the desired outcome.

In an embodiment, the method comprises the provision of an objective measure for fitting the pulse-shape, which may rely on recording the nerve response after its stimulation or any evoked neural response produced by the stimulation.

A Fitting System:

In an aspect, a fitting system configured to estimate the extent of the spread of excitation of different parameterized time-varying waveforms as defined in the method of operating a method of operating a hearing assistance device described above is furthermore provided by the present disclosure. Thereby, a predefined knowledge of corresponding parameterized time-varying waveforms and spread of excitation can be (e.g. stored in a memory of the hearing assistance device, and) utilized in the hearing assistance device to adapt the current stimuli to the current input signal.

A Method Determining a Parameterized Time-Varying Waveform:

In an aspect, a method of determining a temporal pattern of a stimulation waveform is provided by the present disclosure. The method comprises providing a model of ionic currents present in a nerve or neuron, from which the temporal pattern of current to deliver can be computed so that a specific discharge probability and/or temporal accuracy can be obtained; the method comprising one or more of the following steps:

Computing the first passage time probability density using a parameterized pulse shape model.

Computing the set of fibres, which are activated by a single pulse of parameterized temporal shape.

Computing the interactions between sub-sequent pulses in a pulse train.

A Hearing Assistance System:

In a further aspect, a hearing assistance system comprising a hearing assistance device as described above, in the 'detailed description of embodiments', and in the claims, AND an auxiliary device is moreover provided.

In an embodiment, the system is adapted to establish a communication link between the hearing assistance device and the auxiliary device to provide that information (e.g. control and status signals, possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the function of a remote control is implemented in a SmartPhone, the SmartPhone possibly running an APP allowing to control functionality of the hearing assistance device via the SmartPhone (the hearing assistance device(s) comprising an appropriate wireless interface to the SmartPhone, e.g. based on Bluetooth or some other standardized or proprietary scheme).

In an embodiment, the auxiliary device is another hearing assistance device. In an embodiment, the hearing assistance system comprises two hearing assistance devices adapted to implement a binaural hearing assistance system, e.g. a binaural hearing aid system.

Definitions:

In general, a "hearing assistance device" refers to a device, such as e.g. a hearing aid or a listening device, which is adapted to improve, augment and/or protect the hearing capability of a user by receiving acoustic signals from the user's surroundings, generating corresponding (electric) audio signals, possibly modifying the audio signals, and providing the possibly modified audio signals as audibly sensed signals to at least one of the user's ears, e.g. (as in the present disclosure) in the form of electric signals transferred directly or indirectly to the cochlear nerve, to other sensory nerves and/or to the auditory cortex of the user.

The hearing assistance device according to the present disclosure may be configured to be worn in any known way (including an implanted part), e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

In some hearing assistance devices, the output unit may comprise one or more output electrodes for providing electric signals. In some hearing assistance devices, the output electrodes may be implanted in the cochlea and/or on the inside of the skull bone and may be adapted to provide the electric signals to the hair cells of the cochlea, to one or more auditory nerves and/or to the auditory cortex and/or to other parts of the cerebral cortex.

A "hearing assistance system" refers to a system comprising a hearing assistance device and another device in communication with the hearing assistance device. A "binaural hearing system" refers to a system comprising two hearing devices and being adapted to cooperatively provide audible signals to both of the user's ears. In a hearing assistance system or a binaural hearing assistance system, one or both of the hearing assistance devices may comprise other output means in addition to output electrodes in order to provide audible signals e.g. in the form of acoustic signals radiated into the user's outer ears or acoustic signals transferred as mechanical vibrations to the user's inner ears through the bone structure of the user's head and/or through parts of the middle ear. In such hearing assistance devices, the output unit may comprise an output transducer, such as e.g. a loudspeaker for providing an air-borne acoustic signal or a vibrator for providing a structure-borne or liquid-borne acoustic signal. In a binaural hearing system, the output electrodes may be omitted in one hearing device comprising such other output means.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which:

FIG. 5A) arriving at a neuron of the cochlear nerve and the probability of discharging the neuron (cf. FIGS. 7A-7C shows a combined illustration of the spatial range of excited neurons for two different stimulation pulse waveforms, a square waveform as shown in FIG. 3A and a positively sloped waveform according to the present disclosure as shown in FIG. 5D, FIG. 7A schematically illustrating waveforms of the positively sloped stimulation pulses as seen by neurons located at various locations to both sides of the (single, mono-polar) stimulated electrode ($E_z$), FIG. 7B schematically illustrating a spatial current spread caused by the stimulation pulse at the stimulated electrode ($E_z$), and FIG. 7C schematically illustrating a corresponding spatial spread of neuron excitation caused by the stimulation current.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
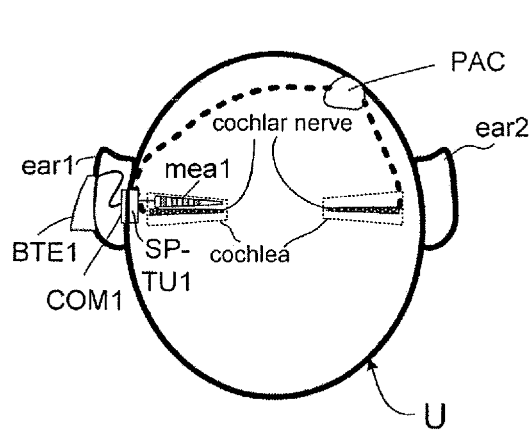
FIGS. 1A-1C shows a use case of a hearing assistance device comprising an implanted part according to the present disclosure, FIG. 1A schematically showing the head of a user wearing the device, FIG. 1B schematically showing a cross section of cochlea including a multi electrode array of the device, FIG. 1C schematically showing a perspective cross-sectional view of cochlea with the multi electrode array is mounted in scala tympani.
Figure 1B:
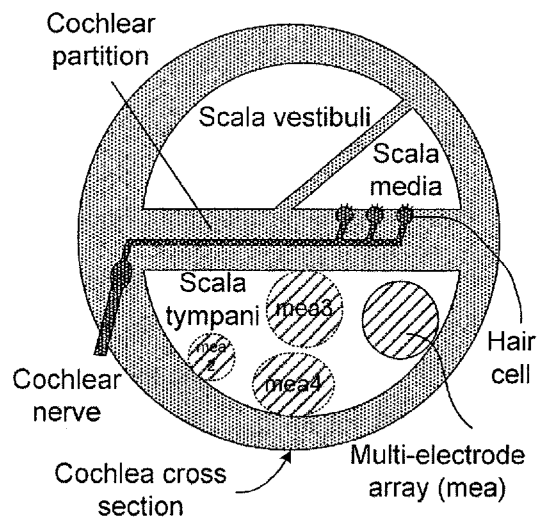
Figure 1C:
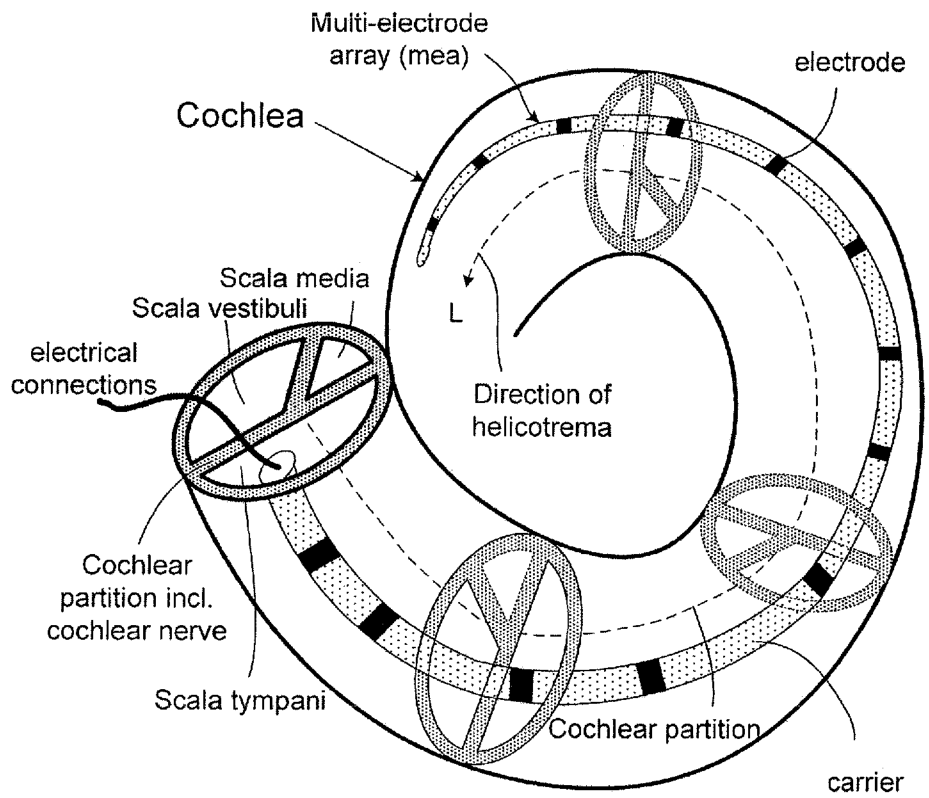

FIGS. 1A-1C shows a use case of a hearing assistance device comprising an implanted part according to the present disclosure.

FIG. 1A illustrates a monaural hearing assistance system comprising a single hearing assistance device of the cochlear implant type located at a right ear (ear1) of a user (U). Other embodiments may comprise a bilateral (or binaural, or hybrid solutions, e.g. comprising two implanted electrodes and one common processor) system wherein a hearing assistance device is located at each of the ears (ear1, ear2) of a user (U), the two hearing assistance devices being optionally in communication with each other in that they each comprise a transceiver for establishing a (wireless or wired) link between them allowing the transmission and reception of information to/from the other device. The hearing assistance device comprises an external part and an implanted part. Likewise, a hearing assistance system according to the present disclosure may additionally comprise any other multi-electrode-array stimulation, alone or combined with any other acoustic or vibrator-based stimulation on the same ear or the other. The external part is adapted to be located at or in an ear of the user and comprises in the embodiment of FIG. 1A a sound capture and processing part (BTE1) adapted to be located behind an ear of the user (U), and a communication part (COM1) in operational communication with the sound capture and processing part (BTE1), here via a wired connection. The communication part (COM1) is configured to communicate with the implanted part, including to transfer information about a current electric stimulus (e.g. representative of a current sound signal picked up by the sound capture and processing part (BTE1)) to be applied to the cochlear nerve (cochlear nerve). The cochlear nerves are connected to the auditory centre of the brain (the Primary Auditory Cortex, denoted PAC in FIG. 1A) as indicated by the bold dashed lines. The implanted part comprises a communication and stimulation unit (SP-TU1) and a multi-electrode array (mea1) in operational communication with each other. The communication and stimulation unit (SP-TU1) is configured to exchange information with the communication unit (COM1) of the external part, including to receive stimulation information, and to generate corresponding stimulation pulses, and to apply such pulses to electrodes of the multi-electrode array (mea1).

The multi-electrode array (mea, mea1) may comprise a flexible, originally substantially linearly shaped carrier with a number of individually electrically accessible electrodes located along the length of the carrier. In an embodiment, the flexible carrier is configured to adapt to the form of cochlea when inserted. Alternatively, the multi-electrode array (mea, mea1) may (semi-rigidly) be pre-shaped to the form of cochlea.

FIG. 1B schematically shows a cross section of cochlea including a multi electrode array of the hearing assistance device. The multi-electrode array (mea) is in the transversal cross-sectional view of cochlea of FIG. 1B located at an inner wall in the right side of scala tympani. It may, however, be located other places in the scala tympani (e.g. as indicated by electrodes (mea2, mea3, mea4) having a dotted outline). Further, the multi-electrode array may be located elsewhere in proximity of the cochlear nerve (e.g. in one of the other scala). The three scala of cochlea, Scala tympani, Scala media and Scala vestibuli, are schematically illustrated and denoted by the same names in FIG. 1B. The cochlear partition (Cochlear partition) hosting (a part of) the cochlear nerve (Cochlear nerve) and separating the Scala media and Scala vestibuli from the Scala tympani, is schematically indicated in FIG. 1B. The cochlear nerve comprises hair cells (Hair cell) reaching into Scala media.

FIG. 1C schematically shows a perspective cross-sectional view of cochlea (Cochlea) with the (exemplary location of) multi electrode array (mea) being mounted in scala tympani (Scala tympani). The multi electrode array (mea) comprises a carrier (carrier) comprising a number of electrodes (electrode), e.g. 8 or more, distributed along its length (cf. dashed arrow denoted L (length) and indicating a Direction of helicotrema, where Scala tympani and Scala vestibuli meet). Each electrode (electrode) is configured to provide the option of electrical stimulation of a particular part of the cochlear nerve as indicated by the bold line denoted electrical connections in FIG. 1C. The electrical connections are operationally connected to the stimulation unit (SP-TU1) in FIG. 1A (or similarly to unit STU-MEU-PU-CONT in FIG. 8).

For some clinical cases of profound deafness with non-implantable cochlea (e.g., fully ossified, Mondini syndrome, etc.) or non-stimulable cochlear nerve (e.g., nerve cut following Neurofibromatosis acoustic tumor surgery), the hearing assistance device may comprise electrodes placed on the auditory brainstem, i.e. beyond the cochlear nerve and before the auditory cortex. The present disclosure comprises such embodiments where the hearing assistance device is an auditory brainstem implant.

Figure 2A:
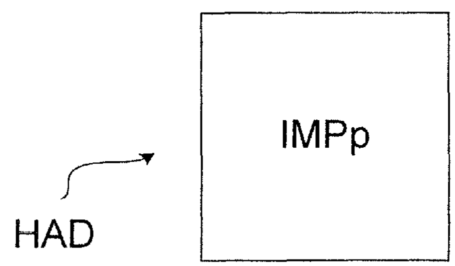
FIGS. 2A-2C shows various partitions of a hearing assistance device according to the present disclosure; the embodiment in FIG. 2A comprising only an implanted part, the embodiment in FIG. 2B comprising an implanted part and an external part with a wireless communication link between them, and the embodiment in FIG. 2C comprising the same elements as the embodiment of FIG. 2B, but where the external part comprises an antenna part for establishing the wireless link to the implanted part and a processing part for processing an audio signal, and where the antenna and processing parts are connected by a wired link, FIGS. 3A-3E schematically shows elements of a neural response to an exemplary spatial stimulation pulse excited at a (single, mono-polar) location ($L_z$) along the cochlear nerve, FIG. 3A showing the exemplary (prior art) bi-phasic square symmetric waveform stimulation pulse with a time delay between the positive and negative phases of the pulse, the positive and negative pulses having equal height and width, FIG. 3B illustrating stimulation of neurons along the cochlear nerve due to stimulation of a single specific electrode ($E_z$) at location $L_z$, FIG. 3C schematically showing exemplary waveforms of the stimulation pulses as seen by neurons located at various locations to both sides of the stimulated electrode ($E_z$), FIG. 3D schematically illustrating a spatial current spread caused by the stimulation pulse at the stimulated electrode ($E_z$), and FIG. 3E schematically illustrating a corresponding spatial spread of neuron excitation caused by the stimulation current, FIGS. 4A-4D schematically shows three examples of mono-polar and multi-polar stimulation schemes, FIG. 4A illustrating the (multi-array) stimulation electrode(s) spatially distributed along a cochlear nerve, FIG. 4B illustrating a mono-polar stimulation of electrode $E_z$ with a bi-phasic pulse, FIG. 4C illustrating a first multi-polar stimulation comprising stimulation of electrode $E_z$ with a positive pulse and neighbouring electrodes $E_{z+1}$ and $E_{z-1}$ with negative pulses, and FIG. 4D illustrating a second multi-polar stimulation comprising stimulation of electrode $E_z$ with bi-phasic pulse and neighbouring electrodes $E_{z+1}$ and $E_{z-1}$ with corresponding bi-phasic pulses of opposite phase.
Figure 2B:
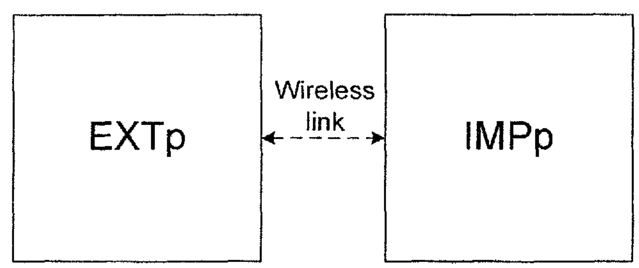
Figure 2C:
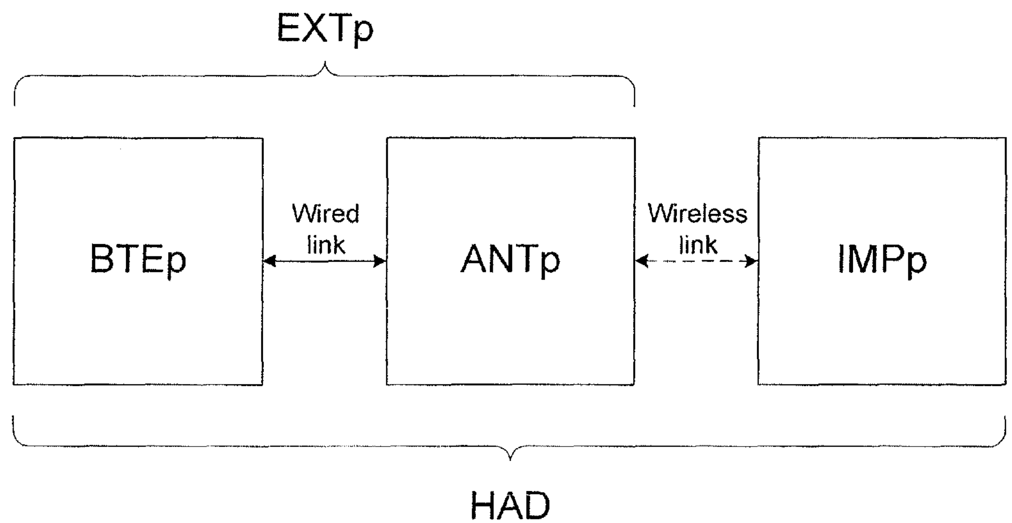

FIGS. 2A-2C shows various partitions of a hearing assistance device according to the present disclosure.

FIG. 2A shows a hearing assistance device (HAD) in its most basic form comprising only a, preferably self-contained (e.g. battery driven, and comprising an input transducer, e.g. a microphone, and appropriate processing capability), implanted part (IMPp). FIG. 2B shows a hearing assistance device (HAD) comprising an implanted part (IMPp) and an external part (EXTp) with a wireless (e.g. inductive) communication link (Wireless link) between them. The external part (EXTp) may e.g. comprise an input transducer, e.g. a microphone, and a signal processing unit for enhancing a received electric input signal and possibly for preparing a scheme for stimulating electrodes of the implanted part (IMPp) in dependence of the current input signal. The external part (EXTp) may further comprise antenna and transceiver circuitry for transferring stimulation information (and possibly corresponding energy) to the implanted part (IMPp) (which comprises corresponding antenna and transceiver circuitry to allow reception of the transmitted signals and energy, to establish the Wireless link). Alternatively, the link from the external part (EXTp) to the implanted part (IMPp) may be based on a wired connection. FIG. 2C shows a hearing assistance device (HAD) as in FIG. 2B but where the external part (EXTp) comprises an antenna part (ANTp) for establishing the wireless link to the implanted part (IMPp) and a processing part (BTEp) for processing an audio signal, and where the antenna and processing parts are connected by a wired link (Wired link, e.g. a cable). In an embodiment, the processing part (BTEp) is configured to be located at an ear of the user. Alternatively, the processing part (BTEp) and the antenna part (ANTp) may be connected by a wireless link. This may be particularly relevant, if the processing part (BTEp) is located elsewhere than at an ear of the user.

FIGS. 3A-3E shows elements of a neural response to an exemplary spatial stimulation pulse excited at a (single, mono-polar) location ($L_z$) along the cochlear nerve.

Figure 3A:
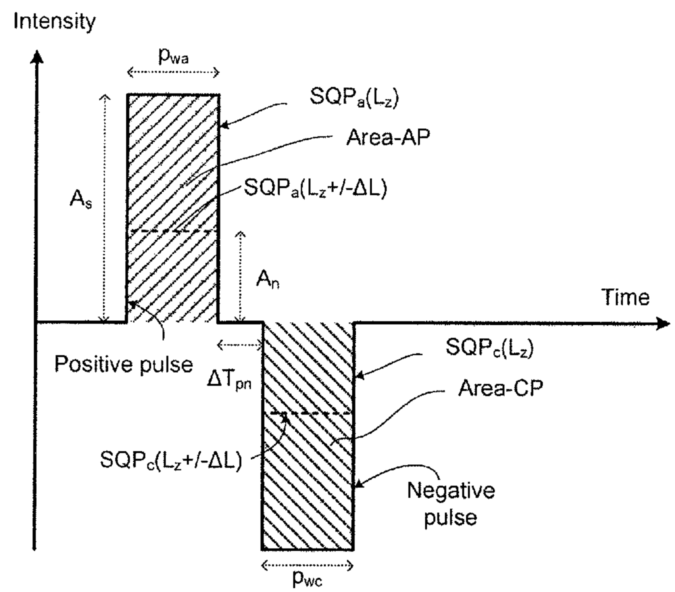

FIGS. 3A-3E schematically illustrates how excitation of neurons spreads around an electric stimulation intended to stimulate a specific location (area) of the cochlear nerve in an exemplary electrical stimulation of a cochlear implant, for which a multi-electrode array (mea in FIGS. 3B-3C) produces a stimulation (of bi-phasic symmetric, square pulse shape, cf. FIG. 3A).

FIG. 3A shows an exemplary time-variant, (prior art) bi-phasic, square symmetric waveform stimulation pulse with a time delay ($\Delta T_{pn}$) between the positive ($SQP_a$) and negative ($SQP_c$) phases of the pulse, the positive (Positive pulse) and negative (Negative pulse) pulses having equal height ($A_s$) and width ($p_{wa}=p_{wc}$) to conserve charge neutrality (as indicated by the areas enclosed by the respective pulses being equal: Area(AP)=Area(CP)). The time variant waveforms are drawn in an amplitude (Intensity, e.g. charge density or current (e.g. in units of A)) versus time (T) plot.

Figure 3B:
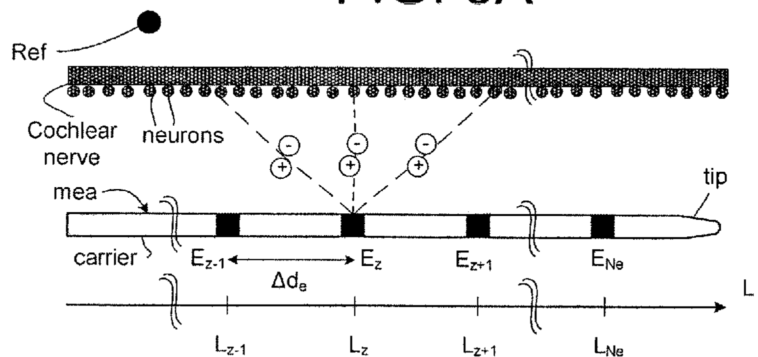

The solid line bi-phasic, symmetric stimulation pulse of FIG. 3A (denoted $SQP_a(L_z)$, $SQP_c(L_z)$) exhibits a square waveform of a given amplitude ($A_s$, intensity, e.g. charge/phase) at the location ($L_z$) of the neurons intended for receiving pulses from the electrode in question (cf. $E_z$ in FIG. 3B). When a given stimulation pulse arrives at neurons located a distance ($L_z$+/−ΔL) away from the target neurons the amplitude (intensity) of the square pulse has been modified (decreased to $A_n$, cf. dashed waveforms $SQP_a$ ($L_z$+/−ΔL) and $SQP_c$($L_z$+/−ΔL) in FIG. 3A for the positive and negative phases, respectively).

FIG. 3B schematically illustrates stimulation of neurons (neurons) along the cochlear nerve (Cochlear nerve) due to stimulation of a single specific electrode ($E_z$) at location $L_z$. The current provided by the stimulation pulse(s) is indicated by ions (encircled +, − signs, respectively, in FIG. 3B). A multi-electrode array (mea) is schematically shown along the cochlear nerve with an accompanying length indication (arrow L) increasing towards the (rounded off) tip (tip) of the carrier. Electrodes $E_{z-1}$, $E_z$, $E_{z+1}$, . . . , $E_{Ne}$, where $N_e$ is the number of electrodes on the carrier (carrier), are spaced apart, e.g. according to a scheme adapted to a particular user, or to a general user. In an embodiment, the electrodes are regularly spaced by a predefined distance ($\Delta d_e$). A reference electrode (Ref), e.g. to pick up charges during a mono-polar stimulation is shown. The reference electrode is preferably located outside cochlea.

Figure 3C:
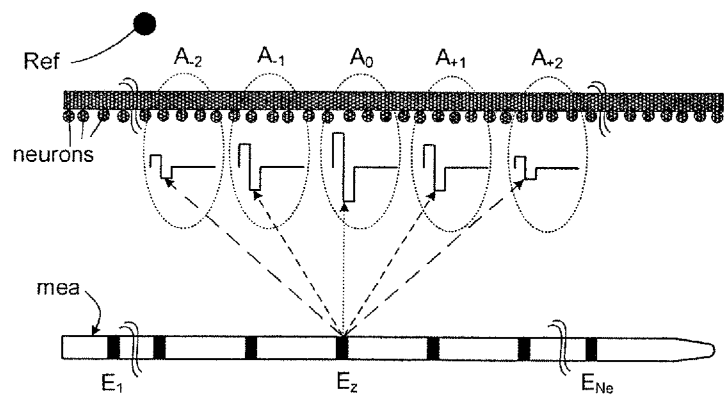

FIG. 3C schematically shows exemplary waveforms of the stimulation pulses as experienced by neurons located at various locations to both sides of the stimulated electrode ($E_z$). The amplitude of the stimulation pulses is decreasing with increased distance from the stimulated electrode, as indicated by the graphs in dotted elliptical enclosures below the neurons (neurons) of the cochlear nerve in FIG. 3C. Corresponding amplitudes of the pulses are denoted $A_{-2}$, $A_{-1}$, $A_0$, $A_{-1}$, $A_{+2}$, respectively.

Figure 3D:
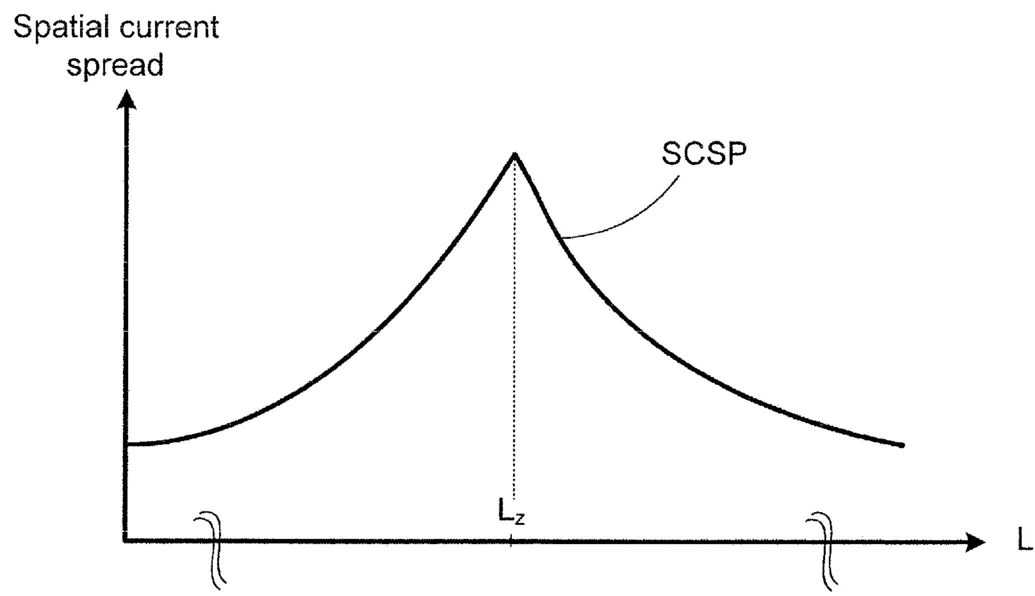
Figure 3E:
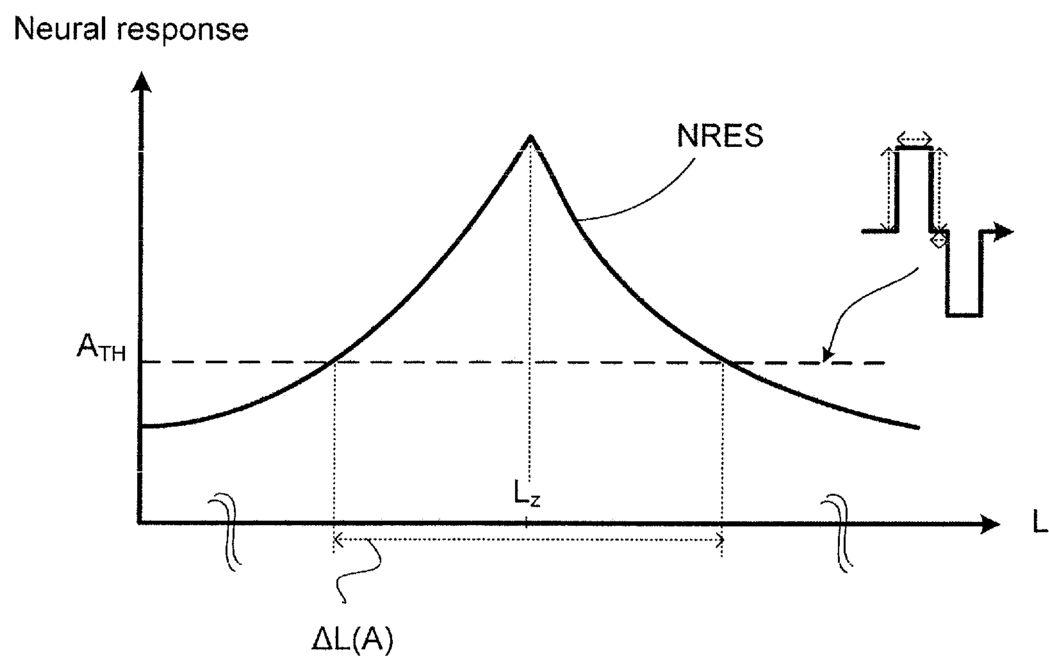

FIG. 3D schematically illustrates a spatial current spread (SCSP) caused by the stimulation pulse at the stimulated electrode ($E_z$ in FIG. 3B, 3C). The graph in FIG. 3D shows current versus distance (L) with a decrease in current to both sides of a maximum at the location $L_z$ of the stimulating electrode. FIG. 3E schematically illustrates a corresponding spatial spread of neuron excitation (Neural response) caused by the stimulation current. The graph in FIG. 3E shows neural response (NRES) versus distance (L) with a decrease in response to both sides of a maximum at the location $L_z$ of the stimulating electrode. A threshold value $A_{TH}$ indicates a level below which the neurons will not discharge. A corresponding spatial spread $\Delta L(A)$ around the location $L_z$ of the stimulating electrode is indicated. The threshold value $A_{TH}$ (and hence the spatial spread $\Delta L(A)$ of the neural response) depends on characteristics of the stimulation pulse, as indicated by the graphical insert of the bi-phasic, symmetric, square waveform associated with the dashed line indicating the threshold value $A_{TH}$.

In the example of FIGS. 3A-3E, a mono-polar stimulation using a single stimulation electrode ($E_z$) and a reference electrode (Ref) is assumed. Further, a bi-phasic, symmetric square stimulation pulse is used for illustration. However, bi-polar (or multi-polar in general) stimulation and/or single phase (positive) or asymmetric stimulation may just as well be used (cf. FIGS. 4A-5F). According to the present disclosure, a positively sloped positive stimulation pulse is preferably used (cf. FIGS. 5A-5F). As indicated in FIG. 3C, the pulses experienced by neurons farther away from the stimulated electrode ($E_z$ in FIGS. 3A-3E) decrease in amplitude with distance from the stimulated electrode (cf. ($A_i$, i=−2, −1, 0, +1, +2), but may still be large enough to be perceived by (i.e. to excite or fire) neurons at such locations, as illustrated in FIG. 3D, 3E.

Figure 4A:
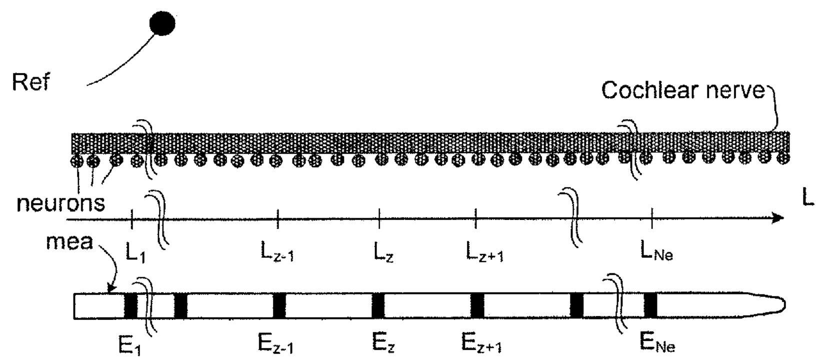
Figure 4B:
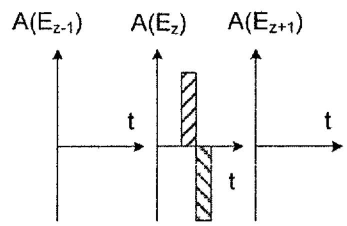
Figure 4C:
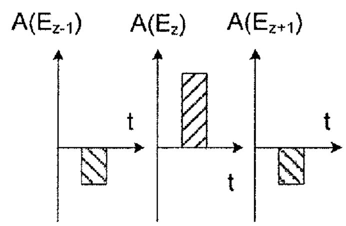
Figure 4D:
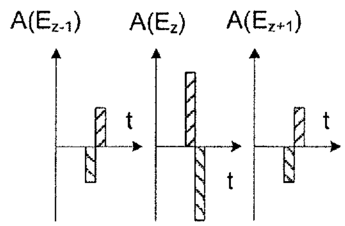

FIGS. 4A-4D shows three examples of mono-polar and multi-polar stimulation schemes. FIG. 4A illustrates the (multi-electrode array) stimulation electrode(s) (mea) spatially distributed (L) along a cochlear nerve comprising neurons (neurons) to be stimulated. A reference electrode (Ref) for use in mono-polar stimulation is further shown. FIG. 4B illustrates a mono-polar stimulation of electrode $E_z$ with a bi-phasic pulse (utilizing reference electrode Ref for the return current) in an amplitude $A(E_z)$ versus time t plot. FIG. 4C illustrates a first multi-polar (asymmetric) stimulation comprising stimulation of electrode $E_z$ with a positive pulse ($A(E_z)$ versus time t) and stimulating neighbouring electrodes $E_{z+1}$ and $E_{z-1}$ with negative pulses ($A(E_{z+1})$ and $A(E_{z-1})$, respectively, versus time t). To conserve charge balance, the total charge of the combined negative phases of stimulation pulses at electrodes $E_{z+1}$ and $E_{z-1}$ is equal to the charge of the positive stimulation pulse at electrode $E_z$ (as indicated by the corresponding (hatched) areas of the pulses). FIG. 4D illustrates a second multi-polar stimulation comprising stimulation of electrode $E_z$ with bi-phasic pulse and neighbouring electrodes $E_{z+1}$ and $E_{z-1}$ with corresponding bi-phasic pulses of opposite phase. Again, charge neutrality is intended as indicated by equality of the total areas of the positive phases and the total areas of the negative phases, respectively. The above stimulation schemes are only examples of mono-polar and multi-polar stimulation. Any mono-polar and multi-polar stimulation scheme (providing charge neutrality) may be used in combination with the stimulation waveform according to the present disclosure.

From a general stimulation point of view (spatial and temporal definitions), the polarity will change due to both temporal and spatial definition. I.e., a positive temporal waveform definition can be inversed with polarity inversion of the electrode from a spatial definition criterion, in other words, physically inversed.

FIGS. 5A-5F shows six different exemplary bi-phasic stimulation 'pulse' waveforms according to the present disclosure and their modification at a neuron located spatially apart from the primary target neurons of the electrode emitting the stimulation pulse(s).

Figure 5A:
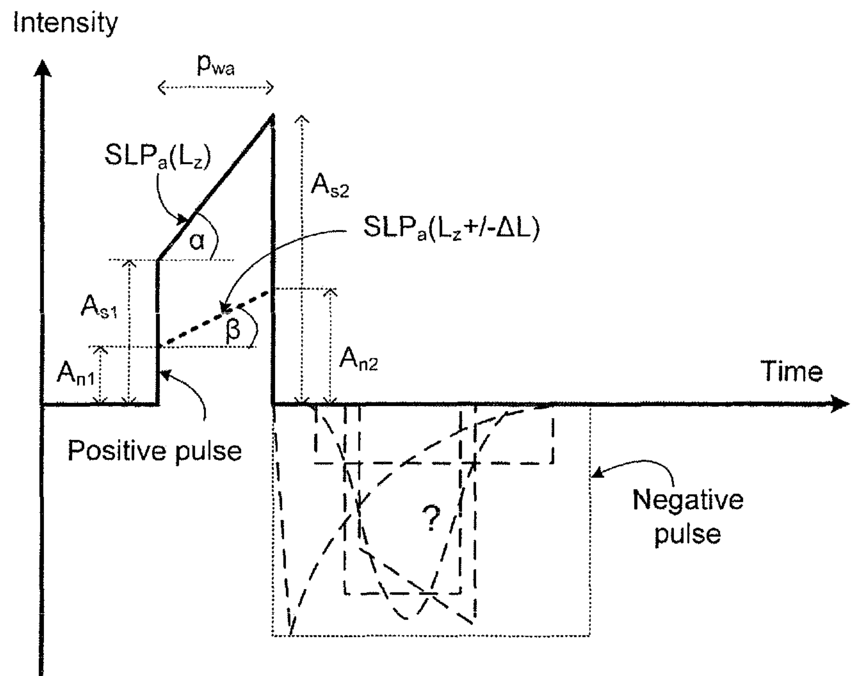
FIGS. 5A-5F shows six different exemplary bi-phasic stimulation 'pulse' waveforms according to the present disclosure and their modification at a neuron located spatially apart from the primary target neurons of the electrode emitting the stimulation pulse(s), FIG. 5A showing a stimulation pulse comprising a positive sloped pulse according to the present disclosure and an arbitrary negative pulse (or none), FIG. 5B showing a bi-phasic asymmetric waveform stimulation pulse comprising a positive sloped pulse according to the present disclosure and a square negative pulse, FIG. 5C showing a bi-phasic asymmetric waveform stimulation pulse as in FIG. 5B, but wherein the positive and negative pulses have different widths, FIG. 5D showing a bi-phasic sloped, symmetric waveform stimulation pulse according to the present disclosure, FIG. 5E showing a bi-phasic asymmetric waveform stimulation pulse comprising a positive positively sloped (triangular) pulse according to the present disclosure and a square negative pulse, and FIG. 5F showing a bi-phasic sloped (triangular), symmetric waveform stimulation pulse according to the present disclosure, FIGS. 6A-6B schematically shows in FIG. 6A an exemplary (step-like) relationship between the slope of a positively sloped (positive) pulse (cf. e.g.

FIG. 5A shows a parameterized time-varying waveform (Intensity versus Time) comprising a positively sloping positive pulse stimulation pulse according to the present disclosure and an arbitrary negative pulse (or none). The (optional) negative pulse is shown in the dotted box denoted Negative pulse. A number of purely exemplary waveforms of the (optional) negative pulse are indicated in dashed line in the dotted box, including a passive discharge waveform. The parameterized time-varying waveform of the positive pulse (Positive pulse, $SLP_a(L_z)$, solid line waveform in FIG. 5A) comprises a positively sloped waveform defined by heights of the rising ($A_{s1}$) and falling ($A_{s2}$) edges of the positive pulse (resulting in slope angle $\alpha$) at the location ($L_z$) of stimulation. The positive pulse has a width in time of $p_{wa}$. When a given positive stimulation pulse arrives at neurons located a distance ($\Delta L$) away from the target neurons the amplitudes and the slope of the sloped pulse has been modified (both decreased, to ($A_{n1}$, $A_{n2}$) and $\beta$, respectively, cf. dashed line waveform $SLP_a(L_z+/-\Delta L)$ in FIG. 5A). In general, the width of the positive pulse ($p_{wa}$) is adapted to the current application (and possibly dynamically adapted to the current need for stimulation in the frequency range aimed at by a particular electrode). In an embodiment, the width of the positive pulse is of the order of tens of microseconds. In an embodiment, the width of the positive pulse is larger than 5 μs. In an embodiment, the width of the positive pulse is smaller than 100 μs. The negative pulse(s) is preferably configured to maintain charge neutrality together with the positive pulse(s). The negative pulse(s) may—together with the positive pulse—form part of a biphasic pulse in a mono-polar stimulation configuration, or may be applied to another electrode in a multi-polar stimulation configuration (cf. e.g. FIGS. 4A-4D).

Figure 5B:
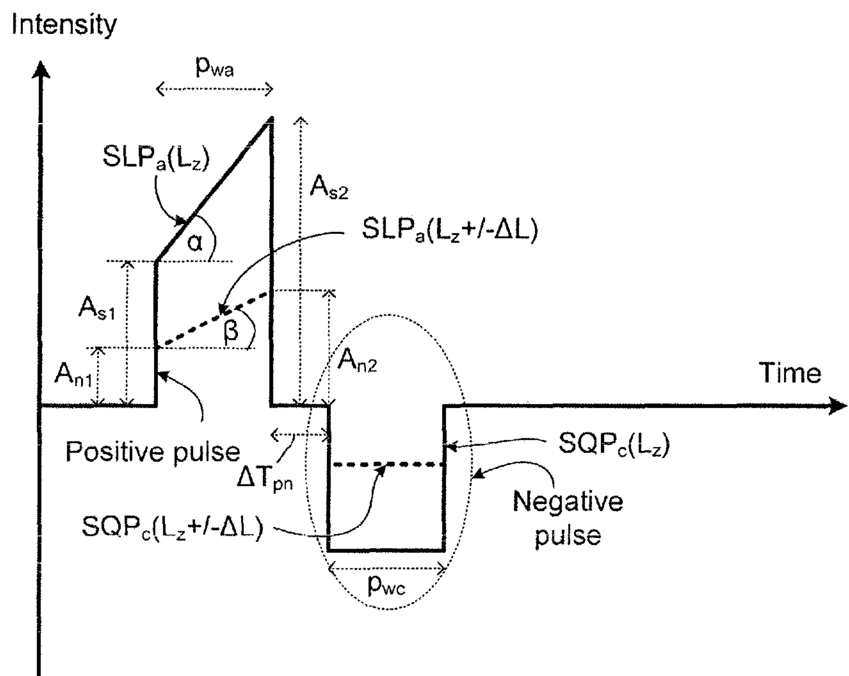

The parameterized time-varying waveform stimulation pulse of FIG. 5B is bi-phasic and asymmetric in that it comprises different positive and negative pulse waveforms. The positive stimulation pulse (Positive pulse, $SLP_a(L_z)$, solid line waveform) exhibiting a positively sloped waveform is equal to that of FIG. 5A. The negative stimulation pulse (Negative pulse, $SQP_c(L_z)$, dashed line waveform) is a square pulse. The pulse width ($p_{wc}$) of the negative phase is equal to the pulse width ($p_{wa}$) of the positive phase. Preferably, the area (charge) of the positive and negative pulses are equal (or a difference is otherwise compensated for, e.g. by multi-polar stimulation). The positive and negative phases are separated by a time delay $\Delta T_{pn}$. In an embodiment, the time delay is zero (see e.g. FIG. 5C).

Figure 5C:
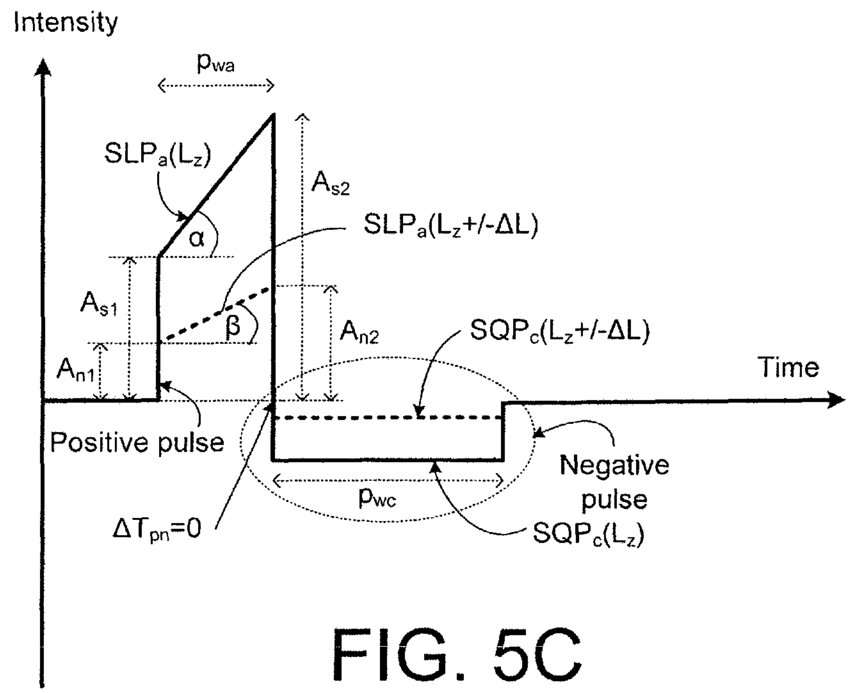

FIG. 5C shows a bi-phasic asymmetric waveform stimulation pulse as in FIG. 5B, but wherein the positive and negative pulses have different widths ($p_{wa}<p_{wc}$) and where the time delay between the positive and negative phases is minimal (e.g. intended to be zero). Again, preferably, the area (charge) of the positive and negative pulses are equal.

Figure 5D:
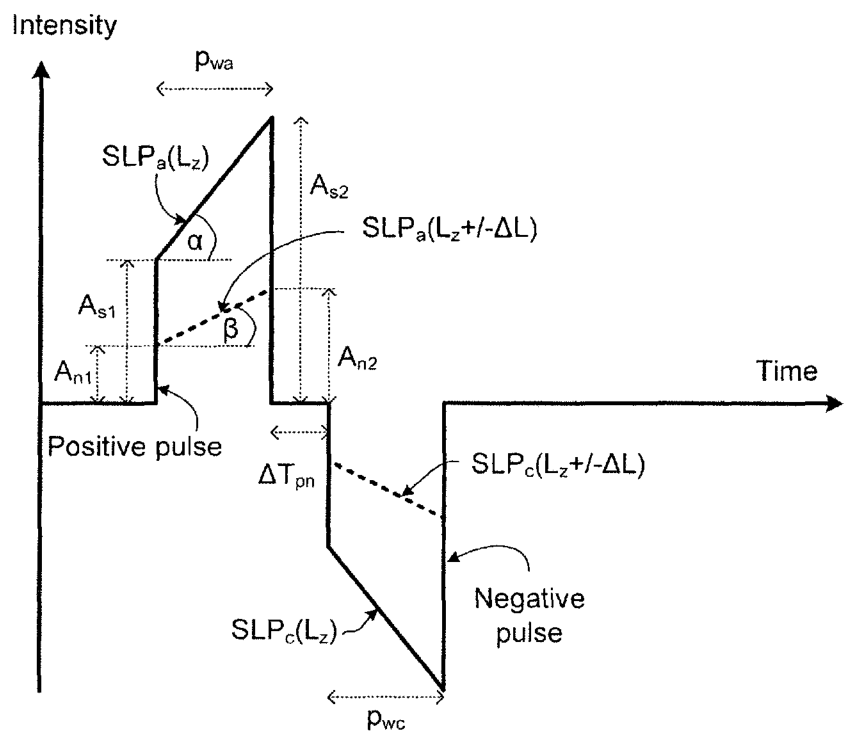

FIG. 5D shows a bi-phasic sloped, symmetric waveform stimulation pulse according to the present disclosure comprising an arbitrary time delay ($\Delta T_{pn}$) between the positive and negative phases of the bi-phasic pulse. The positive pulse is as shown in FIGS. 5A, 5B and 5C, and the negative pulse is a symmetrically generated version thereof (e.g. mirrored around a horizontal axis). Hence, the area (charge) of the positive and negative pulses are equal, thereby preserving charge neutrality.

Figure 5E:
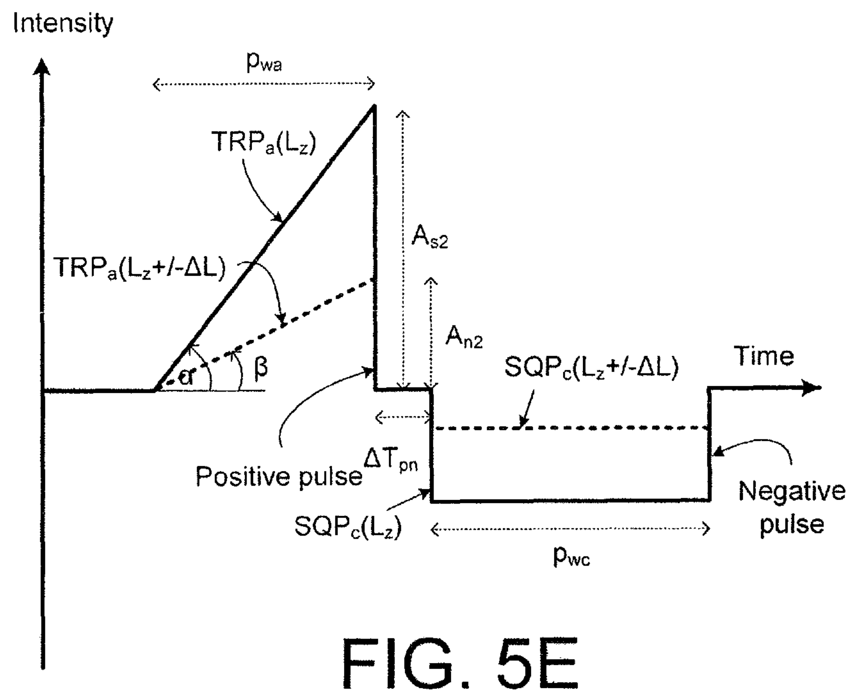

FIG. 5E shows a bi-phasic asymmetric waveform stimulation pulse comprising a positive positively sloped (triangular) pulse $TRP_a(L_z)$ according to the present disclosure and a square negative pulse $SQP_c(L_z)$ comprising an arbitrary time delay ($\Delta T_{pn}$) between the positive and negative phases of the bi-phasic pulse. The triangular pulse is a special case of the parameterized time-varying waveform stimulation pulse of FIG. 5A, where the vertical rising edge is absent ($A_{s1}=A_{n1}=0$). Otherwise, it behaves as previously described, e.g. in connection with FIG. 5A. As in FIG. 5C, the positive and negative pulses have different widths ($p_{wa}<p_{wc}$). Again, preferably, the area (charge) of the positive and negative pulses are equal.

Figure 5F:
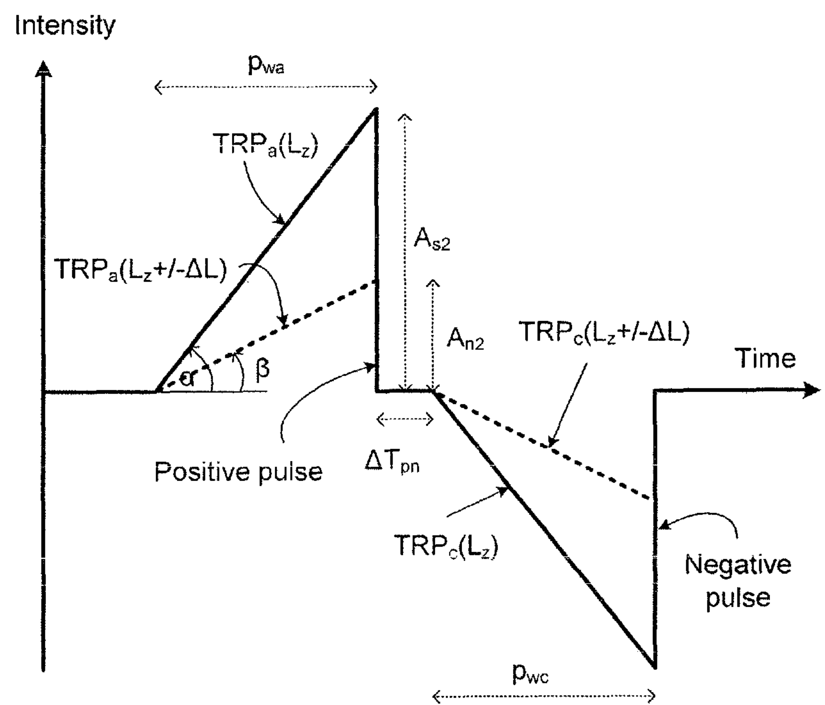

FIG. 5F shows a bi-phasic sloped (triangular), symmetric waveform stimulation pulse according to the present disclosure comprising an arbitrary time delay ($\Delta T_{pn}$) between the positive and negative phases of the bi-phasic pulse. The positive pulse is a triangular pulse as shown in FIG. 5E and the negative pulse is a symmetrically generated version thereof. Hence, the area (charge) of the positive and negative pulses are equal, thereby preserving charge neutrality.

To summarize FIGS. 5A-5F: According to the present disclosure, an important property of the stimulation pulse is the temporal shape of the positive phase. A possible time lag between the positive and negative phases and the waveform of the negative phase are of minor importance. An advantage of the present, sloped stimulation pulse scheme is that it allows to use a variation of slope to code for intensity. Square pulses allow intensity coding too. Preferably, a combination of a square pulse and a triangular pulse (here termed a 'sloped pulse', cf. FIG. 5B, 5C, 5D) can be used. A slope could be a constantly rising current as shown in FIGS. 5A-5F, or a fast succession of flat and rising current like a stair, or any other appropriate increase of the intensity from a lower start value to a higher end value.

The goals are:

to reduce the spatial current spreading (improve spatial selectivity)

to improve intensity coding (e.g. have same amplitude coding with less energy using sloped instead of square pulses).

For sloped pulses (cf. FIGS. 5A-5F), a neuron located a distance from the neuron(s) intended for stimulation sees a smaller pulse. However, in addition to a smaller amplitude of the pulse, the slope of the pulse (stimulating current) has also decreased.

It is assumed that neurons in the auditory system are sensitive to the rate of depolarization. This means that they will discharge only if the slope of stimulation is higher than a certain value. This is assumed to be due to the presence of a fast activating sub-threshold potassium channel.

Figure 7A:
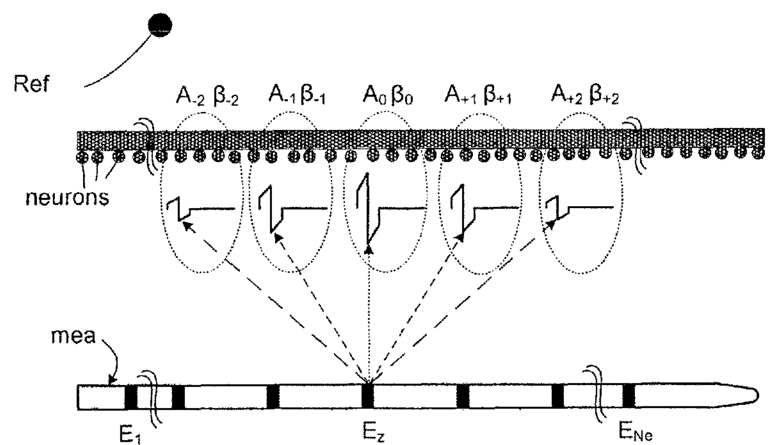
FIGS. 7A-7C), while FIG. 6B illustrate exemplary stimulation pulse slopes having values below and above a threshold slope $SL_{TH}$, respectively.
Figure 7B:
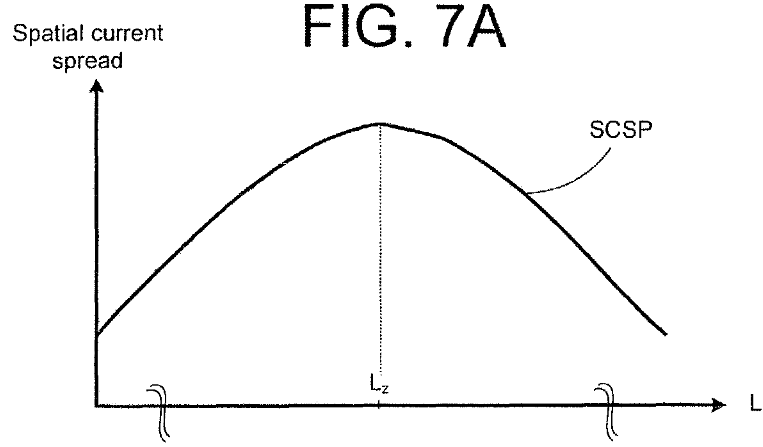
Figure 7C:
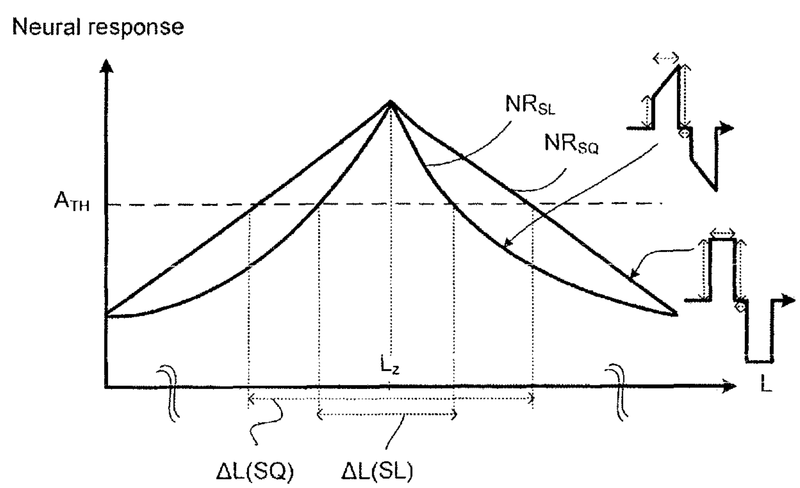

Because of this rate threshold, using a pulse with ramp (a sloped pulse) in its temporal profile will allow to reduce the stimulation spatial selectivity (as illustrated in FIGS. 7A-7C).

Figure 6A:
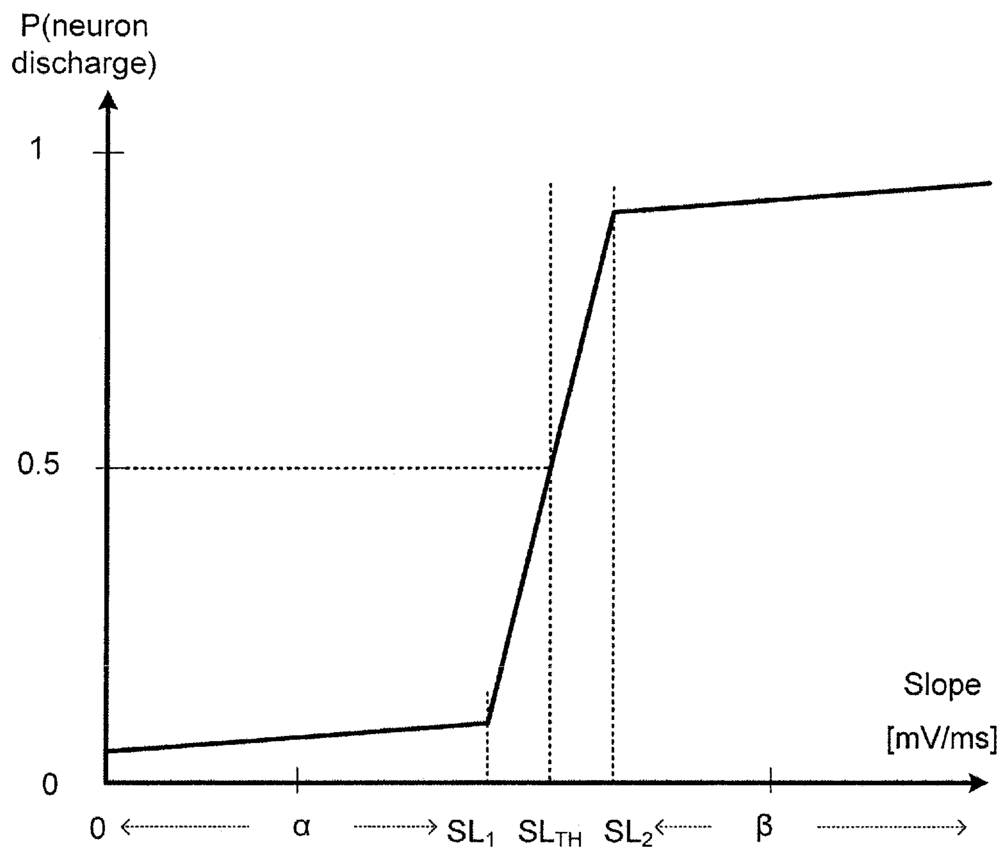
Figure 6B:
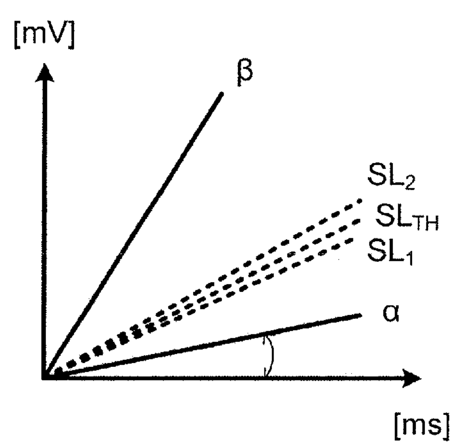

FIGS. 6A-6B shows in FIG. 6A an exemplary (step-like) relationship between the slope of a positively sloped (positive) pulse (cf. e.g. FIG. 5A) arriving at a neuron of the cochlear nerve and the probability of discharging the neuron (cf. FIGS. 7A-7C), while FIG. 6B illustrate exemplary stimulation pulse slopes having values below and above a threshold slope SLTH, respectively. It is believed that the observed property of neurons in the auditory system to be dependent on the slope of the stimulation pulses is linked to the presence of the (low voltage activated) potassium (K+) current $I_{KLVA}$.

FIGS. 7A-7C is a combined illustration of the spatial range of excited neurons for two different stimulation pulse waveforms, a square waveform as shown in FIG. 3A and a positively sloped waveform according to the present disclosure as shown in FIG. 5D. FIG. 7A (corresponding to FIG. 3C dealing with the same issue but for a prior art, square waveform) schematically illustrates waveforms of the positively sloped stimulation pulses as seen by neurons located at various locations to both sides of the (single, mono-polar) stimulated electrode ($E_z$). As also indicated in FIGS. 5A-5F, the amplitudes ($A_i$, i=−2, −1, 0, +1, +2) AND slopes ($\beta_i$, i=−2, −1, 0, +1, +2) of the pulses decrease with increasing distance from the stimulation electrode ($E_z$). FIG. 7B schematically illustrates a spatial current spread (SCSP) caused by the stimulation pulse at the stimulated electrode ($E_z$). The graph in FIG. 7B shows current (SCSP) versus distance (L) with a decrease in current to both sides of a maximum at the location $L_z$ of the stimulating electrode. FIG. 7C schematically illustrates a corresponding spatial spread of neuron excitation (Neural response) caused by the stimulation current by illustrating a probability of neuron excitation along a length of the cochlear nerve centred around a location ($L_z$) of a stimulated electrode ($E_z$) for two different bi-phasic simulation pulse waveforms (as illustrated in FIGS. 3A and 5D, respectively, and indicated by inserts associated with the two different neural response curves), resulting in a different spread ΔL of excitation of neurons for the two waveforms. The threshold value $A_{TH}$ indicating a level below which the neurons will not discharge (dashed line). Corresponding spatial spreads ΔL(SQ) and ΔL(SL) around the location $L_z$ of the stimulating electrode is indicated for each the two stimulation pulse waveforms, square (SQ) and sloped (SL), respectively. As indicated in FIG. 7C, the spatial spread ΔL(SQ) of the neural response of the square stimulation pulse waveforms is larger than the spatial spread ΔL(SL) of the neural response of the sloped stimulation pulse waveforms.

Figure 8:
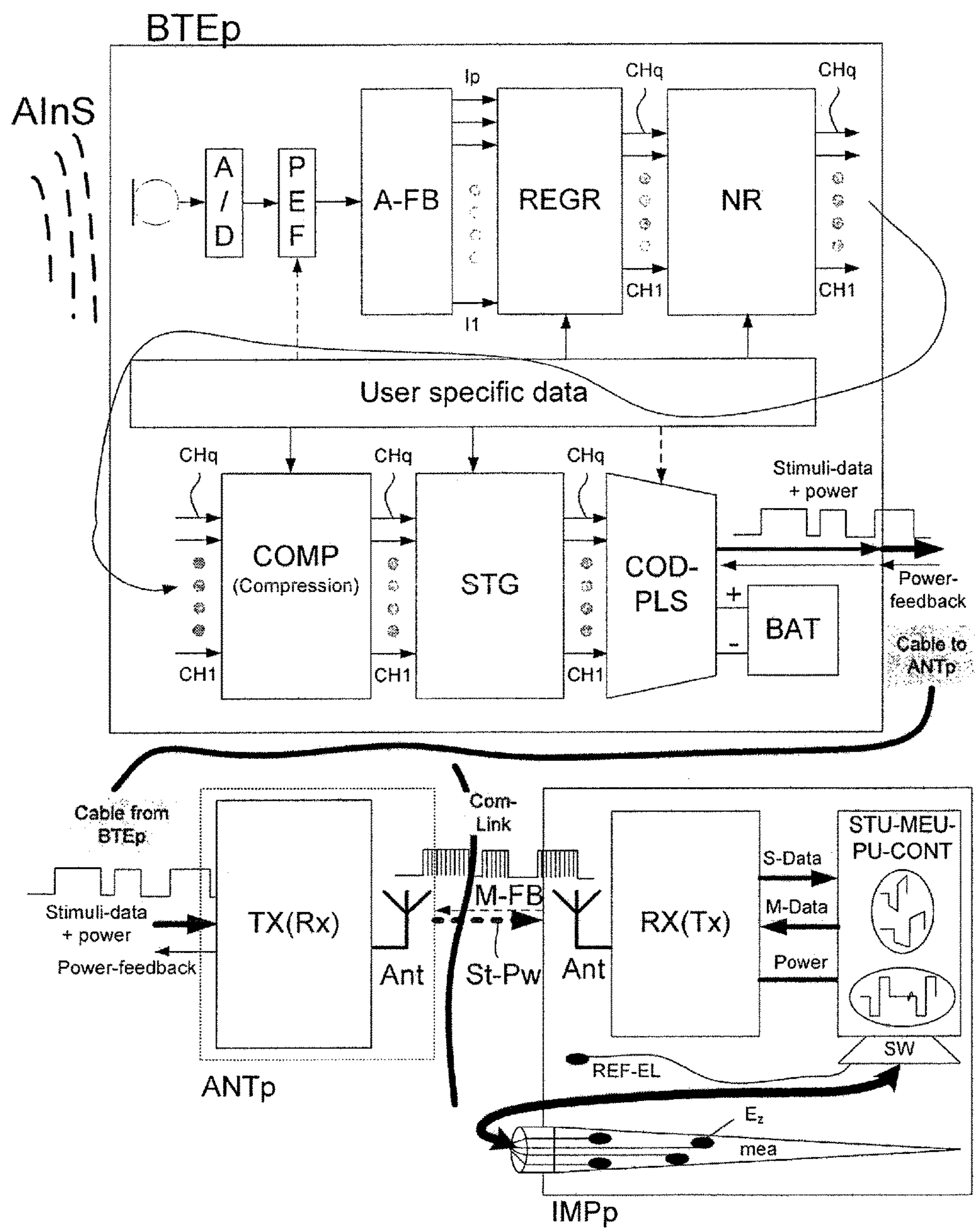
FIG. 8 shows an embodiment of a hearing assistance device comprising an implanted part partitioned as schematically illustrated in FIG. 2C, and FIGS. 9A-9B schematically illustrates two further use cases of a hearing assistance device comprising an implanted part according to the present disclosure, both cases showing a bilateral (or binaural) fitting first and second hearing assistance devices, which may not (bilateral) or may (binaural) be in communication with each other, FIG. 9A showing a use case where each hearing assistance device comprises an implanted part according to the present disclosure, and FIG. 9B showing a use case where one of the hearing assistance devices comprises an implanted part according to the present disclosure, and where the other comprises an output transducer for mechanically or acoustically (e.g. a speaker) providing stimuli interpreted by the user as sound.

FIG. 8 shows an embodiment of a hearing assistance device comprising an implanted part partitioned as schematically illustrated in FIG. 2C. FIG. 8 illustrates a 'normal operation scenario', where electrodes ($E_z$, z=1, 2, . . . , $N_e$) of a flexible multi-electrode array (mea) of the implanted part (IMPp) (inserted into one of the scala of cochlea, e.g. scala tympani, and having its electrodes distributed along the extent of the cochlear nerve). The individual electrodes ($E_z$) are stimulated in dependence of an acoustic input signal (AInS) picked up by a microphone of an external part (EXTp) of the system (cf. FIG. 2B or 2C, here external part BTEp, e.g. adapted for being located behind an ear of a user). In the embodiment of FIG. 8, the relevant current stimulation scheme generated in the external BTEp part and the accompanying necessary electric energy are transferred to the implanted part via a communication link (Com-Link) between the implanted part (IMPp) and an external antenna part (ANTp).

The external BTEp part comprises a forward signal path comprising:

a microphone (or microphone system, e.g. for providing directionality in a specific DIR-mode), an A/D converter (A/D) for converting an analogue input signal to a digital signal by sampling the analogue input signal with a sampling frequency $f_s$, a pre-emphasis filter (PEF) (e.g. a FIR filter) for adapting the input levels to a loudness perception of a normally hearing person (psychoacoustic adaptation), an analysis filter bank (A-FB) for converting a single time variant input signal to time-variant signals in a number p of frequency bands ($I_l$:$I_p$). The analysis filter bank may e.g. comprise a 128 point FFT providing p=64 frequency bands (or alternatively a filter bank followed by an envelope detector), a regrouping unit (REGR) for allocating p frequency bands to a number q of channels ($CH_l$:$CH_q$) equal to the number of electrodes used, e.g. q=20, configurable based on user data (cf. unit User specific data), e.g. based on the Bark scale or 'critical bands'), a noise reduction algorithm (NR, with settings based on User specific data) adapted to attenuate signal components that are judged not to be part of a target signal, the noise reduction algorithm e.g. working independently on signals of each channel ($CH_l$:$CH_q$), a compression scheme (COMP, with settings based on User specific data) adapted to provide a level dependent compression of an input signal of each channel ($CH_l$:$CH_q$), a stimulation generator (STG) for generating a representation of the stimuli corresponding to a given intensity in a given frequency range at a given point in time (reflecting the current input audio signal) to be applied to corresponding electrodes of the implanted part, a local energy source (BAT), e.g. a battery, such as a rechargeable battery for energizing components of the hearing assistance device (BTEp, ANTp, IMPp), and a stimulus data coding unit (COD-PLS, with settings based on User specific data) for generating a scheme (incl. providing energy for stimulating each of the (active) electrodes ($E_z$, max q electrodes, typically less) of the implanted part (IMPp), and forwarding stimuli (or coded stimuli) and energy via a cable to the antenna part (ANTp).

The unit User specific data) may represent user data stored in a memory of the BTEp part or user data read into the various algorithms during a fitting session (or a combination of the two). Such data may include frequency dependent hearing thresholds and uncomfort levels (related to electric stimulation of the individual electrodes). The user specific data may include age, gender, etc.

In an alternative embodiment, the components of the external part (BTEp) are included in the implanted part (IMPp), whereby the hearing assistance device is self-contained (cf. FIG. 2A). In such an embodiment, only a communication link to an external fitting system is necessary.

In the embodiment of FIG. 8, a cable (denoted Cable to ANTp, and Cable from BTEp, in the BTEp- and ANT-p-ends, respectively) connects the BTE-part (BTEp) to the antenna part (ANTp). The cable provides separate digital data and power (denoted Stimuli-data+power) to the antenna part (ANTp).

The antenna part (ANTp) is adapted for being located at the ear of the user allowing a communication link (Corn-link) to be established with the implanted part (IMPp). The antenna part comprises:

a power and data mixing unit (e.g. incl. a crystal oscillator) forming part of an inductive transmitter (and backlink receiver), (TX (Rx)) and antenna coil (Ant).

The implanted part (IMPp) comprises:

an inductive antenna coil (Ant) and receiver (and backlink transmitter), (RX(Tx)), a multi-electrode array (mea) comprising a (typically flexible) carrier (e.g. of silicone rubber) with a multitude of electrodes ($E_z$) (of a corrosion resistant, e.g. noble, metal), each being individually connectable to a current source of a stimulation unit (STU) and preferably a voltage measurement unit for capturing a nerve response by a capacitor:

a stimulation unit (STU) comprising a data extraction circuit, for extracting configuration data and stimuli data a current generator for generating a stimulus current (based on the extracted stimulus data) to be applied to the electrodes ($E_z$), an interface to the electrodes ($E_r$) comprising capacitors and switches (SW) for switching between individual electrodes and their connection to the stimulation unit (STU) and to a measurement unit (MEU), an operational amplifier (e.g. forming part of the measurement unit MEU) and preferably a processing unit (PU) for processing and identifying nerve response measurements (e.g. eCAPs), and a control unit (CONT) configured to control the timing and waveform of the application of stimulation signals in a stimulation time period and the coupling (via switch unit (SW)) of a relevant stimulation electrode to the stimulation unit (STU) and the optional measurement of a resulting response in a measurement time period and the optional coupling (via switch unit (SW)) of a relevant recording electrode to the measurement unit (MEU).

An inductive, preferably bi-directional, communication link (Com-link) (e.g. comprising a 4 MHz carrier) is established by the inductive coils (Ant) of the antenna part (ANTp) and the implanted part (IMPp) when the two are located in an operational position (e.g. near the ear, on each side of the skin of a person). A back-link from the implanted part to the antenna-(and BTE-) part can e.g. be based on 'load communication'. Due to the inductive coupling between the two antenna coils, any draw of current in the implanted part can be sensed in the antenna part. Thereby data-messages can be transmitted to the processor of the BTE-part (e.g. implant status signals (e.g. power level), electrode measurement data (impedances, and eCAPs). The backlink data can e.g. be coded in the signal using pulse width modulation (PWM) or amplitude modulation (AM). Alternatively, a digital coding scheme can be applied The external parts (BTEp and ANTp) can be partitioned in any other appropriate way than shown in FIG. 8. In an embodiment, the outputs of the BTE part (BTEp) are a) digitally coded data representing the electrode stimuli and b) a battery voltage, whereas the antenna part (ANTp) comprises a 4 MHz crystal oscillator whose output is mixed with the coded data to provide an on-off-coded signal, which is transmitted to the implant receiver via the inductive link. In an embodiment, all non-implanted parts of the hearing assistance device are located in a single external device (EXTp) and a communication link (Wireless link) between the implanted and external parts allowing the necessary exchange of information between the two parts (and possibly between the implanted (and/or the external) part and a fitting system), see e.g. FIG. 2B.

In a fitting situation or during operation, nerve responses (e.g. eCAPs) and/or electrode impedance measurements are communicated to a fitting system for setting up the hearing assistance device according to a user's particular needs, either directly via the antenna part (ANTp) or via the BTE part (BTEp).

The analogue electric signal representing an acoustic signal from the microphone is converted to a digital audio signal in the analogue-to-digital converter (A/D). The analogue inputs signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at by a predefined number $N_s$ of bits, $N_s$ being e.g. in the range from 1 to 16 bits. A digital sample x has a length in time of $1/f_s$, e.g. 50 μs, for $f_s$=20 kHz. In an embodiment, a number of audio samples are arranged in a time frame. In an embodiment, a time frame comprises 64 audio data samples. Other frame lengths may be used depending on the practical application.

In an embodiment, the analysis filter bank (A-FB) comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 8 kHz, e.g. 400 Hz to 6 kHz.

Figure 9A:
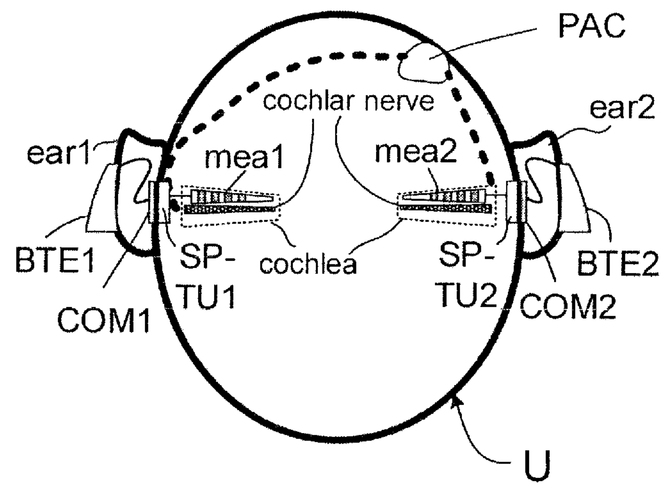
Figure 9B:
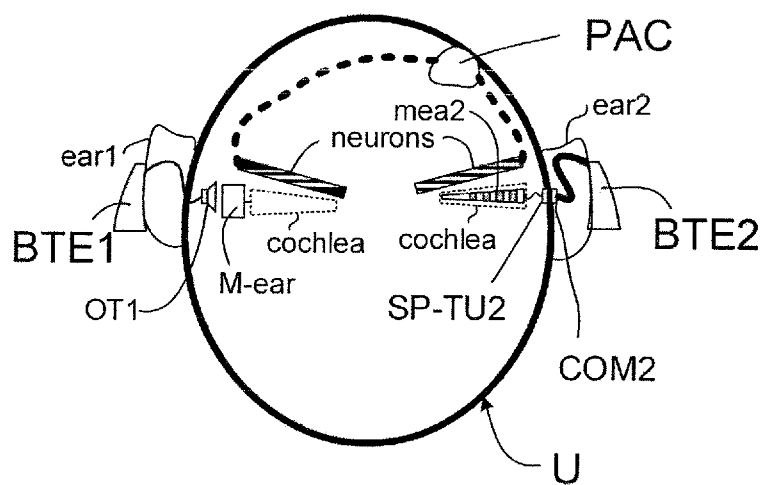

FIGS. 9A-9B schematically illustrates two further use cases of a hearing assistance device comprising an implanted part according to the present disclosure, both cases showing a bilateral (or binaural) fitting first and second hearing assistance devices (which may not (bilateral) or which may (binaural) be in communication with each other). FIG. 9A shows a use case where each hearing assistance device comprises an implanted part according to the present disclosure. The functional parts of the individual first and second hearing assistance devices are discussed in connection with FIG. 1A and FIG. 8. FIG. 9B shows a use case (a so-called bimodal configuration) where one of the hearing assistance devices (the second) comprises an implanted part according to the present disclosure, and where the other hearing assistance device (the first) comprises an output transducer (OTI) for mechanically or acoustically (e.g. a speaker) providing stimuli intended to be interpreted by the user as sound. The output transducer (OTI) of the first hearing assistance device in FIG. 9B is shown as a (loud) speaker for generating acoustic stimuli, but may alternatively or additionally comprise a vibrator for mechanically exciting bones of the user (e.g. the skull). In an alternative embodiment, one of the hearing aid devices may comprise a speaker as well as an implanted part comprising a multi-electrode array. The first hearing assistance device may comprise a normal air conduction type hearing assistance device. The functional parts of the second hearing assistance device (comprising an implanted part) are discussed in connection with FIG. 1A and FIG. 8. The first and second hearing assistance devices may be configured to be able to exchange information between them. In an embodiment, first and second hearing assistance devices each comprises transceiver units allowing a wired or wireless link to be establish between them. An advantage of using a hearing assistance device according to the present disclosure in a bimodal fitting is that is that an improved frequency resolution of the implanted device can be provided to better match the frequency resolution of the corresponding air conduction hearing device.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

U.S. Pat. No. 4,207,441

U.S. Pat. No. 4,532,930

[Clark; 2003] Graeme Clark, Cochlear Implants, Fundamentals and Applications, AIP Press, Springer Science+Business Media, Inc., New York, N.Y., 2003.

[Bal & Oertel; 2001] Ramazan Bal and Donata Oertel, Potassium Currents in Octopus Cells of the Mammalian Cochlear Nucleus, Journal of Neurophysiology, Vol. 86, pp. 2299-2311, Published 1 Nov. 2001

The invention claimed is:

1. A hearing assistance device comprising an implantable part for electrically stimulating an auditory nerve of a user, the implantable part comprising a current source generator;

an electrode array configured to be located inside one of the cochlear scala or adjacent to the auditory nerve, or at the auditory brainstem;

a processor programmed to determine, based on an acoustic input signal picked up by a microphone, a location of the auditory nerve to be stimulated and a spatial range of neurons along the length of the auditory nerve to be excited, calculate a slope of stimulation based on a rate of depolarization associated with the neurons of the auditory nerve and a correlation between the neurons' distances from a stimulation electrode and reductions in slope seen by the neurons, said slope of stimulation being defined as one of:

an amount of charge density over time to be delivered to a singular stimulation electrode in said electrode array to stimulate the determined location of the auditory nerve to be stimulated, and an amount of current over time to be delivered to the singular stimulation electrode in said electrode array to stimulate the determined location of the auditory nerve to be stimulated, and cause said current source generator to deliver to the singular stimulation electrode in said electrode array a time-varying waveform comprising a positive pulse having a rising edge and a falling edge, the positive pulse further having a monotonically increasing segment connecting the rising edge and the falling edge such that an entirety of the positive pulse has a positive slope, the height of the falling edge being larger than the height of the rising edge by an amount that causes the monotonically increasing segment to have the calculated slope of stimulation, thereby causing the singular stimulation electrode in said electrode array to stimulate the determined location of the audio nerve in such manner as to provide a focussed neural excitation based on temporal shaping of a stimulating waveform, wherein said processor calculates the slope of stimulation so as not to exceed a discharge threshold for each neuron of the auditory nerve outside the spatial range thereby preventing a discharge that otherwise would occur to at least one neuron of the auditory nerve based on an amplitude of said pulse in order to improve spectral resolution in the sound perception of the user.

2. A hearing assistance device according to claim 1 wherein said time-varying waveform comprises a negatively sloping negative pulse.

3. A hearing assistance device according to claim 2, wherein the hearing assistance device is a cochlear implant hearing assistance device.

4. A hearing assistance device according to claim 1 wherein the hearing assistance device is configured to dynamically adapt the time-varying waveform to the input signal.

5. A hearing assistance device according to claim 4, wherein the hearing assistance device is a cochlear implant hearing assistance device.

6. A hearing assistance device according to claim 1 wherein the hearing assistance device is configured to provide that the time-varying waveform stimulation pulse is modulated in width and/or amplitude according to the frequency content of the input signal.

7. A hearing assistance device according to claim 6, wherein the hearing assistance device is a cochlear implant hearing assistance device.

8. A hearing assistance device according to claim 1 wherein the time-varying waveform comprises a bi-phasic sloping, symmetric waveform stimulation pulse.

9. A hearing assistance device according to claim 8, wherein the hearing assistance device is a cochlear implant hearing assistance device.

10. A hearing assistance device according to claim 1, wherein the hearing assistance device is a cochlear implant hearing assistance device.

* * * * *